United States Patent
Lin et al.

(10) Patent No.: US 6,745,066 B1
(45) Date of Patent: *Jun. 1, 2004

(54) MEASUREMENTS WITH CT PERFUSION

(75) Inventors: Zhongmin Steve Lin, Solon, OH (US); Scott Kenneth Pohlman, Willoughby, OH (US); Shalabh Chandra, Twinsburg, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 62 days.

This patent is subject to a terminal disclaimer.

(21) Appl. No.: 09/990,352

(22) Filed: Nov. 21, 2001

(51) Int. Cl.[7] ............................................. A61B 5/00
(52) U.S. Cl. ..................... 600/425; 600/420; 600/431; 600/410; 382/131; 382/128; 378/4; 378/62
(58) Field of Search ............................... 600/407, 425, 600/410, 411, 420, 431, 419, 427; 382/128, 131, 132; 378/4, 8, 19, 62; 128/920, 922; 324/307, 309

(56) References Cited

U.S. PATENT DOCUMENTS

| | | | | |
|---|---|---|---|---|
| 5,509,412 A | * | 4/1996 | Bahn ........................... | 600/419 |
| 6,073,042 A | * | 6/2000 | Simonetti .................... | 600/420 |
| 6,381,486 B1 | * | 4/2002 | Mistretta et al. ............. | 600/420 |
| 6,496,560 B1 | * | 12/2002 | Lin et al. ...................... | 378/62 |
| 6,512,807 B1 | * | 1/2003 | Pohlman et al. ............... | 378/4 |
| 6,556,856 B1 | * | 4/2003 | Mistretta et al. ............. | 600/420 |

OTHER PUBLICATIONS

Konig, M., Klotz, E., Heuser, L., Perfusion CT in Acute Stroke.Electromedica 66 (1998), 61–67.*
Miles, K.A., Measurement of tissue perfusion by dynamic computed tomography. The British Journal of Radiology (1991), 64, 409–412.*
Miles, et al. "Functional Computed Tomography", 1997.
Koenig, et al. "Perfusion CT of the Brain: Diagnostic Approach for Early Detection of Ischemic Stroke", Radiology 1998; 209:85–93.
Roberts, et al., "Dynamic CT Perfusion to Assess the Effect of Carotid Revascularization in Chronic Cerebral Ischemic", AJNR 21:421–425, Feb. 2000.
Press, et al. "Numerical Recipes in C", Second Edition, pp. 412–420.
Maes, et al. "Multimodality Image Registration by Maximization of Mutual Information", IEEE Trans. Med. Imag. Vo. 16, No. 2, 1997, pp 187–198.
Holden, et al. "Voxel Similarity Measures for 3–D Serial MR Brain Image Registration", IEEE Trans. Med. Imag. Vo. 19, No. 2, 2000, pp 94–102.
Studholme, et al. "Automated Three–Dimensional Registration of Magnetic Resonance and Positron Emission Tomography Brain Images by Multiresolution Optimization of Voxel Similarity Measures", Med. Phys. 24(1) 1997, pp 25–35.

* cited by examiner

Primary Examiner—Eleni Mantis Mercader
(74) Attorney, Agent, or Firm—Fay, Sharpe, Fagan, Minnich & McKee, LLP

(57) ABSTRACT

A CT scanner (10) for obtaining a medical diagnostic image of a subject includes a stationary gantry (12), and a rotating gantry (14). The detected radiation is reconstructed and divided into sub-portions, which sub-portions are aligned by a registration processor (56). The registered images are stored in a high resolution memory (58) and a maximum artery enhancement value is calculated from the high resolution images. A resolution reducer (82) reduces the resolution of the high resolution images. Time-density curves are found for the voxels of the images, which time-density curves are truncated to eliminate unwanted data, and analyzed to determine characteristic values. A perfusion calculator (106) calculates perfusion by using the maximum artery enhancement value and the characteristic values. A diagnostician can view any one of a low resolution image, a high resolution image, and a perfusion image on a video monitor (112).

24 Claims, 3 Drawing Sheets

MEASUREMENTS WITH CT PERFUSION

BACKGROUND OF THE INVENTION

The present invention relates to the art of medical diagnostic imaging. It finds particular application in conjunction with calculating tissue perfusion using computed tomography (CT) scanners, and will be described with particular reference thereto. However, it is to be appreciated that the present invention is also amenable to other modalities such as MRI, and is not limited to the aforementioned application.

Generally, CT scanners have a defined examination region or scan circle in which a patient, or subject being imaged is disposed on a patient couch. A fan beam of radiation is transmitted across the examination region from a radiation source, such as an x-ray tube, to an oppositely disposed array of radiation detectors. The x-ray tube and associated power supply and cooling components are rotated around the examination region while data is collected from the radiation detectors. Rotation of the radiation source is often achieved by mounting the radiation source to a rotating gantry which is rotated on a stationary gantry. For volume imaging, the patient couch is moved longitudinally. Continuous movement achieves spiral scanning whereas discrete steps achieve a series of parallel slices.

The sampled data is typically manipulated via appropriate reconstruction processors to generate an image representation of the subject which is displayed in a human-viewable form. Various hardware geometries have been utilized in this process. In third generation scanners, both the source and detectors rotate around the subject. In a fourth generation scanner, the x-ray source rotates and the detectors remain stationary. The detector array typically extends 360° around the subject in a ring outside of the trajectory of the x-ray tube.

In a perfusion study, blood flow in tissues and vessels of interest is of primary concern. Typically, a contrast agent is injected into the subject and multiple "snapshots" of the region of interest are taken over time. Present CT scanners are capable of taking 1 to 2 snapshots per second of the region, providing a series of images that tracks the contrast agent in near-real time.

One particular application of CT perfusion is helping to diagnose cerebral ischemia in patients who have suffered acute strokes. This type of study requires precise measurements over a period of time. One technique that is used in the calculation of perfusion is the maximum slope method, which calculates the maximum slope of a time vs. density curve and a maximum arterial enhancement. Perfusion is the maximum slope divided by the maximum arterial enhancement. Accuracy of the quantitative data is impacted by noise in the data, which may have several possible sources. These include patient motion, blood recirculation, partial volume effect, and other factors.

One method of reducing patient motion in a head CT scan, and thus improving the quality of the perfusion investigation, is immobilizing the head of the subject in an external restraint. Typically, such a device includes a strap that is connected to the patient couch that traverses the forehead of the subject, effectively eliminating head motion in a vertical direction (given that the subject is laying horizontally). However, the subject is still capable of movement laterally, as well as slight rotation of the head. These movements can seriously degrade the quality of a perfusion study, causing misalignment of the series of images, blurring a resultant image, and having adverse effects on the calculation of blood perfusion. The maximum density enhancement, measured in Hounsfield units (HU) can be reduced by 40% or more by motion that can occur despite the aid of a head restraint. The blurred images, and effects on perfusion measurements significantly impact the accuracy of quantitative measurements used in diagnosis.

Further, background noise is a factor that affects perfusion calculation, as well as the images associated therewith. Regions that exhibit low signal can be overshadowed by noise. In low blood flow regions, the maximum density enhancement and the noise can both be in the 2–4 Hounsfield unit range. Legitimate perfusion signals can be hidden decreasing the efficacy of the study as a whole. Filters meant to eliminate noise may also eliminate low strength perfusion signals effectively getting rid of good information along with useless information.

The present invention contemplates a new and improved method and apparatus which overcome the above-referenced problems and others.

SUMMARY OF THE INVENTION

In accordance with one aspect of the present invention, a method of perfusion is provided. A region of interest of a subject is disposed in an imaging region of a medical imaging apparatus. A contrast agent is introduced into a bloodstream of the subject. A plurality of images is collected, each image including a plurality of image elements, each image element including an intensity value, the intensity value being a measure of the relative presence of contrast agent in the region. The plurality of images are registered to reduce the effects of subject motion. An artery enhancement curve is plotted.

In accordance with another aspect of the present invention a medical imaging apparatus for obtaining perfusion values is provided. A diagnostic imager gathers a plurality of image slices, each over a period of time. A registration processor corrects for movement of the region of interest over time. An enhancement processor analyzes the slices and determines a peak enhancement time. A filtering processor eliminates unwanted and false data. A resolution reducer combines adjacent pixels of a higher resolution matrix to produce a lower resolution matrix, a dynamic variable calculation processor processes quantities of interest to a diagnostician, and a reconstruction processor formats the matrices into human readable images.

In accordance with another aspect of the present invention, a medical imaging apparatus is provided. A means for generating generates a series of temporally offset slices of a region of interest as a contrast agent moves therethrough. A means for determining determines an evolution of an intensity over time. A means for fitting fits the evolution of the intensity to a model curve. A means for determining determines a maximum intensity, and a means for calculating calculates at least one of perfusion, time to peak, and artery delay values.

One advantage of the present invention is a reduction of the negative effects of patient motion.

Another advantage resides in a reduction of the partial volume effect.

Another advantage resides in the reduction of the negative effects of blood recirculation.

Another advantage resides in the reduction of the effect of low amplitude signals.

Another advantage resides in the increased accuracy of curve fits.

Another advantage resides in reduction of errors caused by noise.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
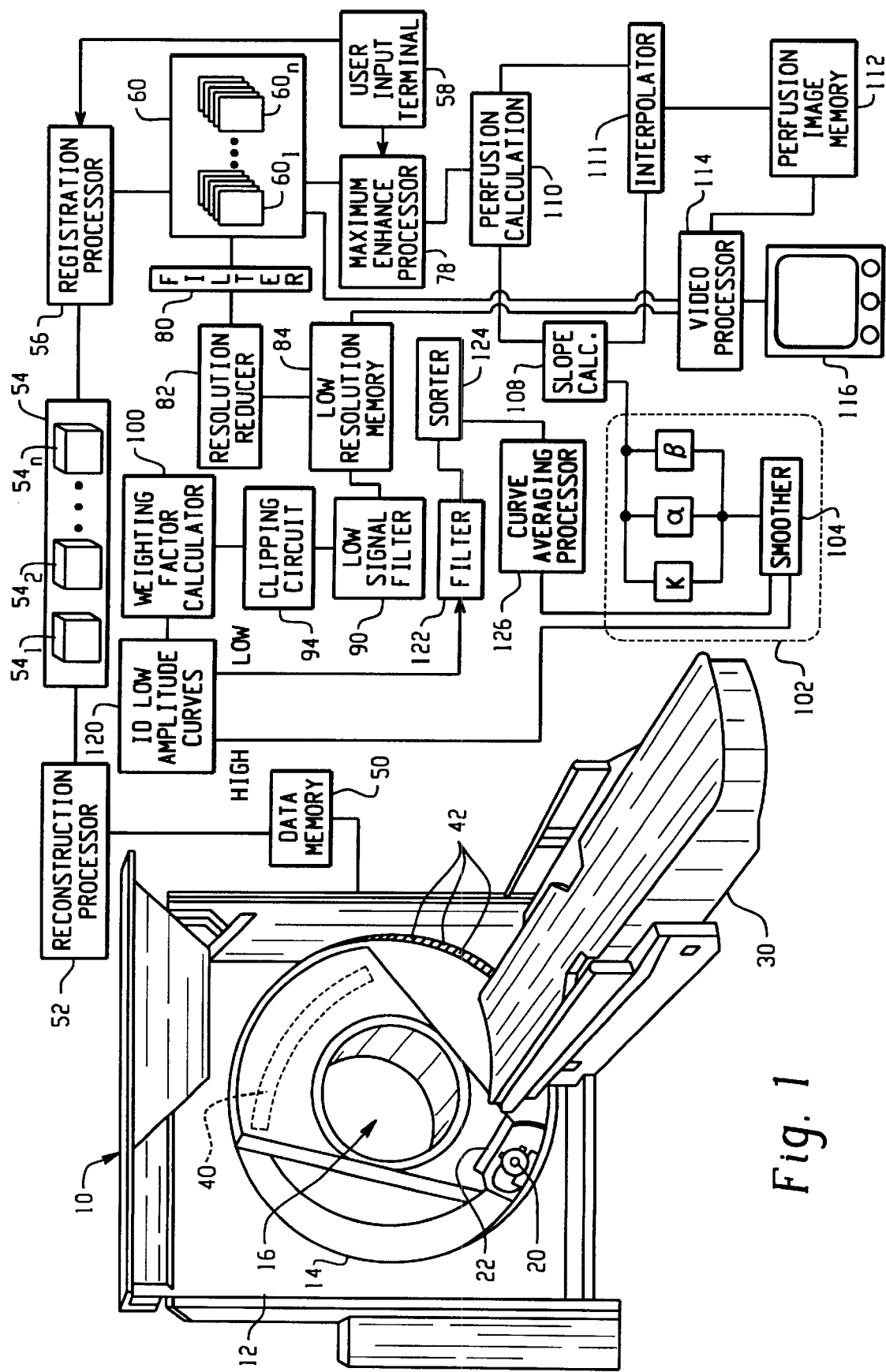
FIG. 1 is a diagrammatic illustration of a computed tomography scanner in accordance with the present invention.

With reference to FIG. 1, a CT scanner 10 includes a stationary gantry 12 and a rotating gantry 14 which define an imaging region 16. The rotating gantry 14 is suspended from the stationary gantry 12 for rotation about the examination region 16. A radiation source 20, such as an x-ray tube, is arranged on the rotating gantry 14 for rotation therewith. The radiation source 20 produces a beam of penetrating radiation that passes through the examination region 16 as the rotating gantry 14 is rotated by an external motor (not illustrated) about a longitudinal axis of the examination region 16. A collimator and shutter assembly 22 forms the beam of penetrating radiation into a cone shape and selectively gates the beam on and off. Alternately, the radiation beam is gated on and off electronically at the source 20. A subject support 30, such as a radiolucent couch or the like, suspends or otherwise holds a subject being examined or imaged at least partially within the examination region 16 such that the cone-shaped beam of radiation defines a volume through the region of interest of the subject.

The imaged volume is repeatedly imaged over a period of time. In a perfusion study, a contrast agent is injected into the subject and factors relating to blood flow of the subject are monitored over a period of time to track blood flow behavior in the region of interest. The volume is segmented into a three dimensional array of voxels, which are often conceptualized as a series of slices, each slice having a finite thickness.

In a third generation CT scanner, an array of radiation detectors 40 is mounted peripherally across from the source on the rotating gantry. In a fourth generation CT scanner, a stationary ring of radiation detectors 42 is mounted around the stationary gantry 12. Regardless of the configuration, the radiation detectors are arranged to receive the radiation emitted from the source 20 after it has traversed the imaging region 16.

The radiation detectors 40, 42 convert the detected radiation into electronic projection data. That is, each of the radiation detectors produces an output signal which is proportional to an intensity of received radiation. Each radiation detector generates data elements which correspond to projections along a corresponding ray within the view. Each element of data in a projection or data line is related to a line integral of an attenuation coefficient taken along its corresponding ray passing through the subject being reconstructed.

A data memory or buffer 50 receives the sampled data from the radiation detectors. The data memory 50 optionally performs filtering or other operations before passing the data to a reconstruction processor 52 which reconstructs volume image representations of the subject.

In the preferred embodiment, the gantry 14 makes approximately 40 turns around the subject, to produce 40 volume images $54_1, 54_2, \ldots 54_{40}$ of the region of interest which are stored in a first series of image memories 54. Of course, the number of images can be more or less, 40 is a balance between factors such as time of scan, radiation dose to the subject, cardiac cycle, and a period of time wherein useful perfusion information can be gathered. Typical present day CT scanners can generate 40 images in about 20–40 seconds, which is a relatively long time that the subject is asked to remain perfectly motionless. In order to correct for inevitable patient motion, a registration processor 56 analyzes the volume images and aligns them such that the region of interest remains stationary over the course of the images.

The registration processor 56 selects a corresponding reference slice in each of the 40 volume images which it actively calculates a movement function. The reference slice is preferably a central slice. In the preferred embodiment, a diagnostician is presented (on a user input terminal 58) with an image of the reference slice. This first image of the reference slice is used as the norm to which each subsequent or preceding time-step image is compared and adjusted to match.

Preferably, the registration processor 56 identifies landmarks which are easy to identify, shapely defined and appear in diverse parts of the slice. In a brain perfusion scan, an exemplary landmark is a portion of the skull, having constant shape and intensity from image to image over the whole scan period. Optionally, the diagnostician can crop the slice to a subregion of interest to reduce processing time.

Each subsequent image of the reference slice is searched in this manner for the selected region, and each subsequent image is shifted or rotated to bring the landmarks into alignment with the reference image. As the registration processor 56 aligns these images, it records a movement function for each of the 40 volume images that describes its movement relative to the reference slice. Especially in a head scan, the region of interest can be considered a rigid body, and any movement that the reference slice undergoes, the entire imaging volume undergoes. The recorded movement function is applied to each slice of the corresponding volume image to align the remainder of the imaging volume. Alternately, and more time intensive, the alignment process can be performed individually for each slice of each volume. Other alignment processes and algorithms are also contemplated.

Some voxels within the region of interest have weak time-density curves. More specifically, some voxels have amplitudes that are comparable with noise. The preferred embodiment groups similar weak signals and combines them to make characteristic stronger signals.

Figure 2:
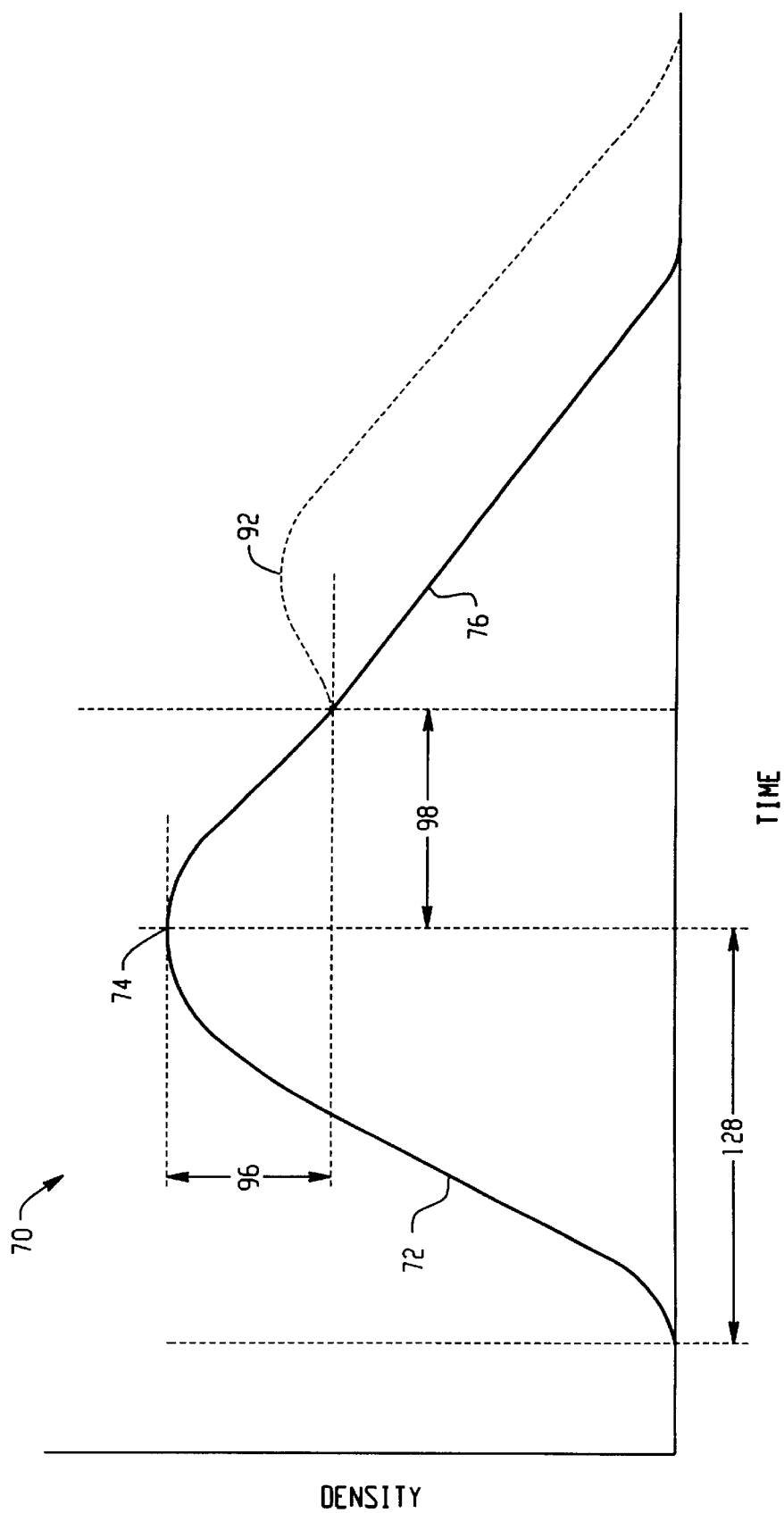
FIG. 2 illustrates a time-density plot for a typical voxel.

After the reconstruction processor 52 has reconstructed the volume images of the region of interest, the volume images are divided into slices and stored in a high resolution slice image memory 60. The slice image memory includes n submemories $60_1, 60_2, \ldots 60_n$, where n is the number of slices in the imaging volume. That is, the first slice of the 40 temporally displaced volume images from the beginning of the scan to the end of the scan are stored in order in a first slice submemory $60_1$, the images of the second slice are stored in a second slice submemory $60_2$, and so on to the images of the $n^{th}$ slice which are stored in an $n^{th}$ submemory $60_n$. In the preferred embodiment, the slices are each one voxel thick. In the preferred embodiment, a 512×512 image matrix is used, and each slice is one voxel thick. That is, the 40 density values from each corresponding voxel in the 40 slices define a time vs. density curve generally as illustrated in FIG. 2. Therefore, in the preferred embodiment in which each slice is 512×512, there are 512×512 time-density curves per slice.

The intensity values of the corresponding voxels of the 40 volume images define a time density curve. Each time density curve is a measure of the amount of contrast agent within the subregion corresponding to the same voxel in each of the time displaced volume images. With reference to FIG. 2, a typical time-density curve 70 includes a leading edge 72 during which the contrast agent is entering the voxel region rapidly, a maximum 74 at which time the contrast agent is at a maximum concentration, and a trailing edge 76 during which the contrast agent is leaving the voxel. The curve typically is a gamma-variate curve which is characterized by its steep leading edge and gradual trailing edge.

A maximum enhancement processor 78 searches for the maximum enhancement value of the time-density curves of the voxels within an artery region indicated by the diagnostician on the reference slice. More specifically, the maximum intensity processor searches for the maximum enhancement among all voxels in a diagnostician indicated artery region. The maximum enhancement of the artery is used later in a perfusion calculation.

The high resolution slices are passed through a filter 80 and subsequently reduced in resolution by a resolution reducer 82. The resolution reducer takes a high resolution image matrix of each slice in time, groups the voxels, and combines each group of voxels, e.g. averages, maximum intensity, etc. In the preferred embodiment, the high resolution matrices are 512×512, and the low resolution matrices are 128×128. The resolution reducer 82 bins the voxels into groups of 16 by position, that is, 4×4 groups of high resolution voxels are combined into a single low resolution voxel. After the volume images over the whole scan time are reduced in resolution, they are stored in a low resolution memory 84.

The low resolution images are used to calculate a number of factors that are later used in the perfusion calculation. More specifically, a low signal filter 90 eliminates low signals. The low signal filter 90 identifies the voxels that have time-density curves too weak or too poorly defined to be used by themselves. At least one of multiple criteria is used to determine which signals are too weak. One method is to compare the time-density curve to a curve model. Voxels having curves outside of a preselected range of fit to the model are discarded as having low signal. Another method is to find a peak enhancement value of the time density curve for each voxel. Voxels with peak enhancements lower than a preselected threshold enhancement value are discarded as having low signal. Another method of identifying low signal voxels is selecting voxels that are historically of low signal, e.g. bone.

Typically, the patient's circulatory system recirculates the contrast agent back through the region of interest causing a secondary intensity peak 92 as shown in phantom in FIG. 2. If the secondary peak is included in the gamma-variate curve fitting, the peak is shifted later in time altering the slope of the leading edge. A clipping circuit 94 clips the secondary peak based on percentage intensity drop 96 from the maximum, a time 98 after the maximum, or a combination of the two. A processor 100 replaces the clipped region with a gamma variate curve segment or other extrapolation of the remaining curve portion. A curve fitting processor 102 compares the time-density curves to a model curve. Data that is not within a preselected tolerance of the ideal curve is filtered out as bad data.

More specifically, a gamma-variate curve smoothing circuit 104 smooths the time density curve of each voxel to reduce noise. The smoothed curves are mathematically fit 106 to a gamma-variate curve. More specifically, the value K, value $\alpha$, and value $\beta$ that define a gamma variate curve mathematically are calculated. Voxels that have a better fit to the gamma-variate model typically have a stronger signal, and are thus more robust for use in the perfusion calculation. A maximum slope calculator 108 calculates the maximum slope of the region 72 of the time-density curve from the K, $\alpha$, and $\beta$ values.

A blood perfusion value is now calculated for each voxel. In a preferred embodiment a perfusion calculator 110 divides the maximum slope value for each voxel by the maximum artery enhancement found the maximum enhancement processor 78 to obtain a perfusion value for each voxel. An interpolator 111 interpolates the truncated time-density curve to form representative curves. Alternately, the K, $\alpha$, $\beta$, and maximum enhancement values can address a preloaded look-up table to retrieve the perfusion value. These values are stored in a perfusion image memory 112. A video processor 114 places data from any one of the low resolution memory 84, the high resolution memory 60, and the perfusion image memory 112 in proper format for a video monitor 116. The high and low resolution images can also be viewed on the monitor 116 in a cinematic image.

Voxels identified as having low amplitude time density curves are identified and sorted by a processor 120. Optionally, the low amplitude data is filtered 122. The filter temporally filters the curves to eliminate curves that are not generally contemporaneous to the curves of neighboring voxels. Alternately or additionally, the curves are filtered based on curve characteristics. Curves that, even though gamma variant in shape, are narrower than a preselected width or which have a slope greater than a preselected shape are removed and replaced with interpolated data. Filtering based on other curve characteristics is also contemplated. The preselected width, slope, and other characteristics are based on a priori knowledge of the characteristics of valid curve characteristics. A sorter 124 sorts the time-density curves into groups. Each group is averaged, or summed, or otherwise combined by a curve averaging processor 126 and the combined time density curve replaces the time density curve of all curves in the group. The sorter 124, in the preferred embodiment, groups the voxels using one of k-means clustering, c-means clustering, and fuzzy logic. It is to be understood that other methods of grouping voxels may also be utilized. The curve averaging processor groups voxels with similar characteristics together. The voxels are determined to be similar based on at least one of its x-coordinate position, its y-coordinate position, its peak enhancement value, a time 128 the time density curve takes to reach the peak enhancement value (time-to-peak), the Hounsfield number, and the like. Once the time density curves are grouped and combined, the groups are passed to the curve fitting processor 102. This greatly reduces the inherent noise in the signals as the noise tends to cancel out as the signals are averaged. Thus, the averaged signal has a higher signal-to-noise ratio than the individual curves of any of the constituent voxels of the group. The curve fitting processor 102 fits the combined time-density curve and fits it to the model curve. A common perfusion value is determined for all the constituent voxels of the group.

For example, the voxels are grouped by x and y-coordinate positions. This scheme yields voxel groups containing constituent voxels that are physically close to each other. In another example, voxels are grouped solely by maximum Hounsfield number, voxels with maximum Hounsfield values of 2–4 HU are grouped together, and voxels with values of 4–8 HU are grouped together, regardless of spatial position. Preferably, the combination of criteria that best serves each individual perfusion study is selected. In this manner, one perfusion image is made from the normal signal voxels and the plurality of low-signal voxel groups.

Figure 3:
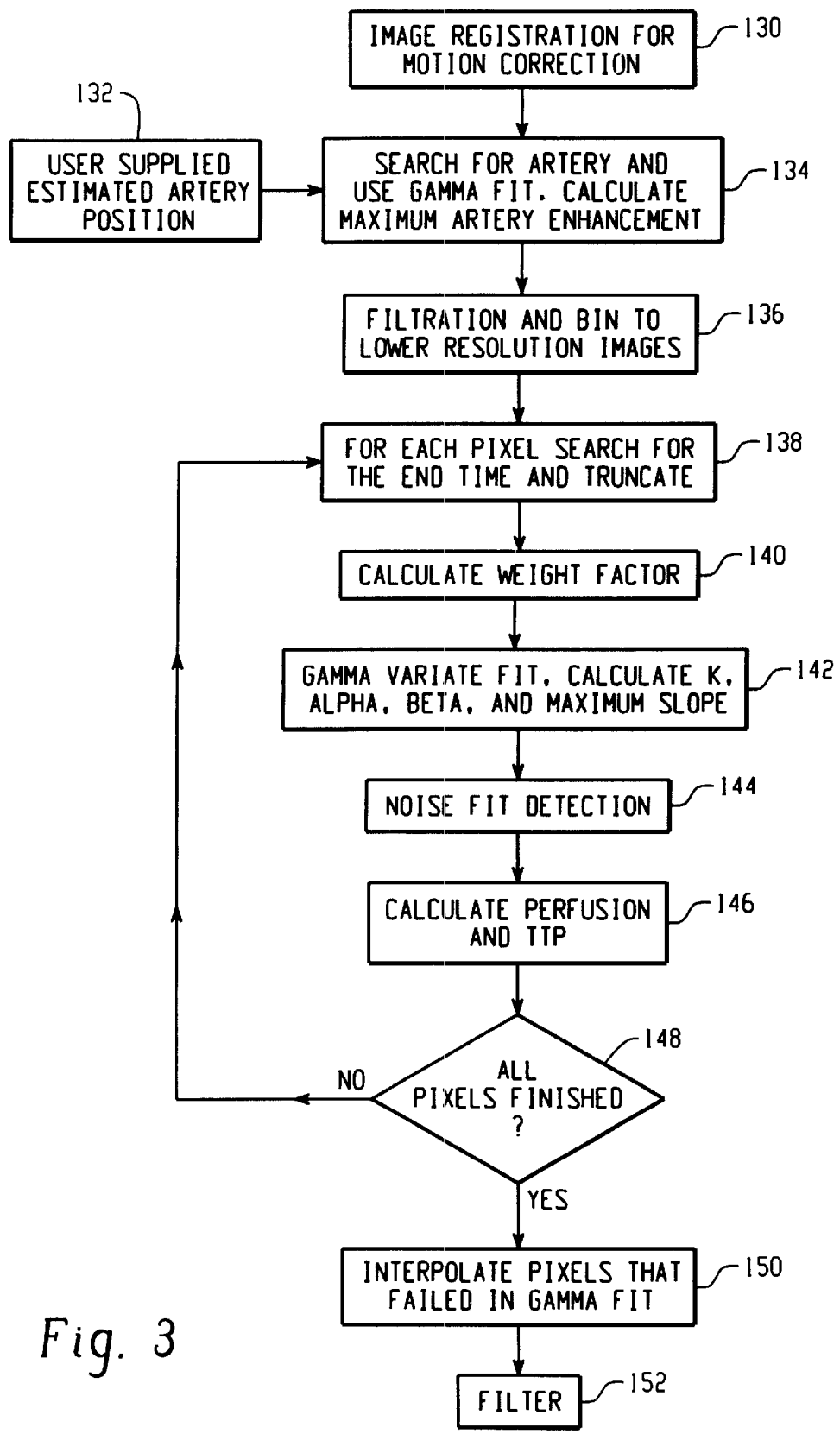
FIG. 3 is a flow diagram that includes integral steps of the present invention.

With reference to FIG. 3, major steps of the preferred embodiment are presented in a flowchart form. In an image registration step 130, the temporally displaced images are aligned with one another. In a user input step 132, the diagnostician estimates the artery position. For example, the diagnostician draws a circle around an artery in the reference slice. In a maximum enhancement calculation step 134, the time-density curves at the designated artery region are examined to find the maximum artery enhancement. In a resolution reducing step 136, the high resolution images are filtered and binned to a lower resolution. In an end time search step 138, the end of usable voxel enhancement data is identified. That is, the density values attribute to the recirculation hump 92 of the time-density curve are normalized as described above. In a weight calculation step 140, the truncated time-density curves are extrapolated. In a curve fitting step 142, the time density curve is fit to a clean gamma variate or other curve model. The characteristic K, α, and β, or other values of the model curve are determined, and maximum slope is calculated. In a noise fit detection step 144, the voxels are searched to identify noise that does not fit a gamma-variate curve. In a perfusion calculation step 146, perfusion value and time-to-peak 128 values are calculated for each voxel. The process is repeated 148 until all of the voxels have been analyzed. In an interpolation step 150, the pixels that failed the gamma fit are assigned a perfusion value by interpolating perfusion values of nearby voxels. In a filtering step 152 the final image is filtered to eliminate excessively bright or dark voxels.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of perfusion imaging comprising:
generating a series of higher resolution temporally offset images of a region of interest, including an artery in or adjacent the region of interest, as a contrast agent moves through the region of interest, said temporally offset images each including a plurality of image elements;
reducing the resolution of the temporally offset images;
for each corresponding image element in the series of reduced resolution of the temporally offset images, determining an evolution of an intensity of the image element over time;
fitting the evolution of the intensity over time to a model curve;
determining a maximum intensity in the artery in or adjacent the region of interest from the higher resolution temporally offset images;
from the model curve fit to each image element and the maximum intensity in the artery, calculating at least one of perfusion, time to peak, and artery delay values for each image element.

2. The method as set forth in claim 1, further including: registering the series of higher resolution temporally offset images to correct for motion of the region of interest.

3. The method as set forth in claim 1, wherein the step of calculating the maximum intensity in the artery includes:
finding the maximum intensity anywhere in a region through which the artery passes.

4. The method as set forth in claim 3, further including:
fitting data in a user designated region to a the model curve, calculating the maximum intensity from a peak amplitude of the model curve.

5. The method as set forth in claim 1, further including before the model curve fitting step:
truncating a time-density curve to eliminate a fluid recirculation portion of the model curve.

6. The method as set forth in claim 5, wherein the step of truncating includes one of:
truncating when the time-density curve has dropped to a preselected percentage of a maximum value; or
truncating a preselected time after the occurrence of the maximum intensity; or
truncating a preselected time after a start of the model curve.

7. The method as set forth in claim 1, further including after the step of fitting:
discarding data that fails to evolve similarly to the model curve.

8. The method as set forth in claim 1, further including after the step of fitting:
determining a weighting factor for each image element from a degree of fit measure to the model curve.

9. The method as set forth in claim 8, further including:
combining perfusion values for a user selected subregion, the perfusion value of each image element being weighted as per the weighting factor.

10. The method as set forth in claim 1, further including:
removing perfusion values greater than a first amplitude and less than a second amplitude and replacing them by interpolating adjacent image elements.

11. The method as set forth in claim 10, wherein the first amplitude is the maximum intensity in the artery, and the second amplitude is a preselected minimum intensity.

12. The method as set forth in claim 1 further including:
filtering the model curves to identify intensity curves representative of invalid data and replacing the invalid data with interpolated data.

13. The method as set forth in claim 12 wherein the filtering includes at least one of:
temporal filtering to identify model curves that represent invalid data by the time at which they occur; and,
curve characteristic filtering to identity model curves that represent invalid data by shape characteristics of the model curve.

14. A method of determining perfusion comprising:
disposing a region of interest of a subject in an imaging region;
introducing a contrast agent into the subject;

collecting a plurality of higher resolution images of the region of interest, each image including an intensity value for each of a plurality of image elements, which intensity values increase as a concentration of the contrast agent in the region of interest increases;

creating lower resolution images from the plurality of higher resolution images;

determining a time-density curve for each image element that represents intensity values vs. time as the contrast agent flows into a subregion of the region of interest corresponding to the image elements of the lower resolution images;

calculating a maximum slope of the time-density curve;

calculating a maximum intensity value in an artery in or near the region of interest from the higher resolution images;

calculating at least one of blood perfusion, time to peak, and artery delay values from the time-density curves and the maximum intensity in the artery.

15. The method as set forth in claim 14 further including:

registering the plurality of higher resolution images to lessen negative effects of subject motion.

16. The method as set forth in claim 14, wherein the step of creating lower resolution images includes:

grouping sets of adjacent image elements;

combining the sets of adjacent image elements by creating one image element that represents each set of adjacent image elements.

17. The method as set forth in claim 14, wherein the step of calculating the maximum intensity in the artery includes:

finding a maximum peak value of the time-density curves in a user designated area.

18. The method as set forth in claim 14, further including:

at an end time, truncating each of the determined time-density curves; and, interpolating a remainder of each time-density curve after the end time.

19. The method as set forth in claim 18, wherein the step of truncating includes one of: truncating the time-density curve at the end time, the end time being when the time-density curve has dropped to a pre-selected percentage of its maximum value; and or, truncating the time-density curve at the end time, the end time being a pre-selected time after a time when the maximum value occurs.

20. The method as set forth in claim 18, further including:

computing a weighting factor for each of the plurality of image elements based in a degree of fit of its time-density curve to a model curve.

21. The method as set forth in claim 14, further including:

filtering data determined to be false from factoring into the blood perfusion calculation.

22. A medical imaging apparatus for perfusion imaging, the apparatus comprising:

a means for generating a series of higher resolution temporally offset images of a region of interest as a contrast agent moves through the region of interest, an artery being in or adjacent the region of interest;

a means for reducing the resolution of the temporally offset images;

a means for determining an evolution of image element intensity over time, for each of corresponding image elements of the series of reduced resolution temporally offset images;

a means for fitting the evolution of intensity over time to a model curve;

a means for calculating a maximum intensity from the higher resolution images;

a means for calculating at least one of perfusion, time to peak, and artery delay values for each image element, from the model curve fit to the corresponding image elements of each of the reduced resolution temporally offset images and the maximum intensity in the artery.

23. The medical imaging apparatus as set forth in claim 22, further including:

a means for truncating the model curve of the intensity over time to eliminate a fluid recirculation portion of the model curve.

24. The medical imaging apparatus as set forth in claim 22, further including:

a means for removing perfusion values greater than a first amplitude and less than a second amplitude and replacing them by interpolating adjacent image elements.

* * * * *